United States Patent
Titus et al.

(10) Patent No.: US 9,827,376 B2
(45) Date of Patent: Nov. 28, 2017

(54) PLUNGER ASSEMBLY INCLUDING A PLUNGER ROD FOR ADVANCING A STOPPER THROUGH A SYRINGE

(71) Applicant: Becton, Dickinson and Company, Franklin Lakes, NJ (US)

(72) Inventors: Noel Titus, New York, NY (US); Yan Yevmenenko, New York, NY (US); Christopher Todd Hilliard, Bath, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 334 days.

(21) Appl. No.: 14/602,789

(22) Filed: Jan. 22, 2015

(65) Prior Publication Data

US 2015/0209521 A1    Jul. 30, 2015

Related U.S. Application Data

(60) Provisional application No. 61/933,058, filed on Jan. 29, 2014.

(51) Int. Cl.
*A61M 5/315*    (2006.01)

(52) U.S. Cl.
CPC .... *A61M 5/31511* (2013.01); *A61M 5/31515* (2013.01); *A61M 2005/31518* (2013.01)

(58) Field of Classification Search
CPC .......... A61M 5/31511; A61M 5/31515; A61M 2005/31518
USPC .............. 604/110, 218, 222, 187; 623/17.11
See application file for complete search history.

(56) References Cited

U.S. PATENT DOCUMENTS

| | | | |
|---|---|---|---|
| 2,895,773 | A | 7/1959 | McConnaughey |
| 3,176,595 | A | 4/1965 | Schwartz |
| 3,809,082 | A | 5/1974 | Hurschman |
| 3,939,833 | A | 2/1976 | Hansson et al. |
| 4,215,701 | A | 8/1980 | Raitto |
| 4,266,557 | A | 5/1981 | Merry |
| 4,354,507 | A | 10/1982 | Raitto |
| 4,363,329 | A | 12/1982 | Raitto |

(Continued)

FOREIGN PATENT DOCUMENTS

| | | |
|---|---|---|
| DE | 2024117 | 9/1971 |
| EP | 0654280 A1 | 5/1995 |

(Continued)

*Primary Examiner* — Manuel Mendez
(74) *Attorney, Agent, or Firm* — The Webb Law Firm

(57) ABSTRACT

Provided herein is a plunger assembly for advancing a plunger through a barrel, such as the barrel of a pre-filled syringe. The plunger assembly includes a stopper adapter defining an aperture. The stopper adapter includes a first restraining member adjacent to the aperture. The plunger assembly also includes a plunger rod having a first end, a second end, and a plunger rod head disposed adjacent the first end of the plunger rod. The plunger rod head includes a second restraining member engageable with the first restraining member of the stopper adapter. The plunger assembly is configured such that as the plunger rod head is moved axially within the aperture of the stopper adapter, the first restraining member of the stopper adapter engages the second restraining member of the plunger rod head to secure the plunger rod head within the aperture. A syringe assembly with a plunger assembly is also disclosed.

23 Claims, 14 Drawing Sheets

(56) References Cited

U.S. PATENT DOCUMENTS

| | | |
|---|---|---|
| 4,500,310 A | 2/1985 | Christinger |
| 4,543,093 A | 9/1985 | Christinger |
| 4,931,043 A | 6/1990 | Ray et al. |
| 4,973,308 A | 11/1990 | Borras et al. |
| 4,986,820 A | 1/1991 | Fischer |
| 5,195,975 A | 3/1993 | Castagna |
| 5,201,709 A | 4/1993 | Capra et al. |
| 5,246,423 A | 9/1993 | Farkas |
| 5,314,416 A | 5/1994 | Lewis et al. |
| 5,395,345 A | 3/1995 | Gross |
| 5,397,313 A | 3/1995 | Gross |
| 5,411,488 A | 5/1995 | Pagay et al. |
| 5,411,489 A | 5/1995 | Pagay et al. |
| 5,496,285 A | 3/1996 | Schumacher et al. |
| 5,531,693 A * | 7/1996 | Vounatsos ............ A61M 5/5066 604/110 |
| 5,554,191 A * | 9/1996 | Lahille ............... A61B 17/1757 411/55 |
| 5,624,405 A | 4/1997 | Futagawa et al. |
| 5,688,252 A | 11/1997 | Matsuda et al. |
| 5,722,951 A | 3/1998 | Marano |
| 5,735,825 A | 4/1998 | Stevens et al. |
| 5,795,337 A * | 8/1998 | Grimard ............ A61M 5/31511 604/222 |
| 5,899,881 A | 5/1999 | Grimard et al. |
| 6,017,330 A | 1/2000 | Hitchins et al. |
| 6,053,894 A | 4/2000 | Shadd, Jr. |
| 6,093,171 A * | 7/2000 | Huang ................. A61M 5/322 604/110 |
| 6,171,286 B1 | 1/2001 | Gross |
| 6,361,524 B1 | 3/2002 | Odell et al. |
| 6,575,938 B2 | 6/2003 | Sayama et al. |
| 6,743,216 B2 | 6/2004 | Odell et al. |
| 6,872,191 B2 | 3/2005 | Lo |
| 6,955,691 B2 * | 10/2005 | Chae ....................... A61F 2/446 623/17.11 |
| 6,991,618 B2 | 1/2006 | Lau et al. |
| 7,056,301 B2 | 6/2006 | Liu |
| 7,081,107 B2 | 7/2006 | Kito et al. |
| 7,111,848 B2 | 9/2006 | Tachikawa et al. |
| 9,533,103 B2 * | 1/2017 | Okihara ............ A61M 5/31515 |
| 2002/0022806 A1 | 2/2002 | Witowski |
| 2004/0006308 A1 * | 1/2004 | Lo ........................ A61M 5/5013 604/110 |
| 2004/0010235 A1 | 1/2004 | Weilbacher et al. |
| 2004/0127859 A1 | 7/2004 | Ward |
| 2005/0154353 A1 | 7/2005 | Alheidt |
| 2007/0088270 A1 | 4/2007 | Cude |
| 2008/0300550 A1 | 12/2008 | Schiller et al. |
| 2012/0136298 A1 | 5/2012 | Bendix et al. |
| 2013/0012888 A1 | 1/2013 | Okihara |
| 2013/0085453 A1 * | 4/2013 | Manke ............... A61M 5/31511 604/218 |

FOREIGN PATENT DOCUMENTS

| | | |
|---|---|---|
| FR | 1500009 | 1/1968 |
| WO | 2005002652 A2 | 1/2005 |
| WO | 2005070485 A1 | 8/2005 |

* cited by examiner

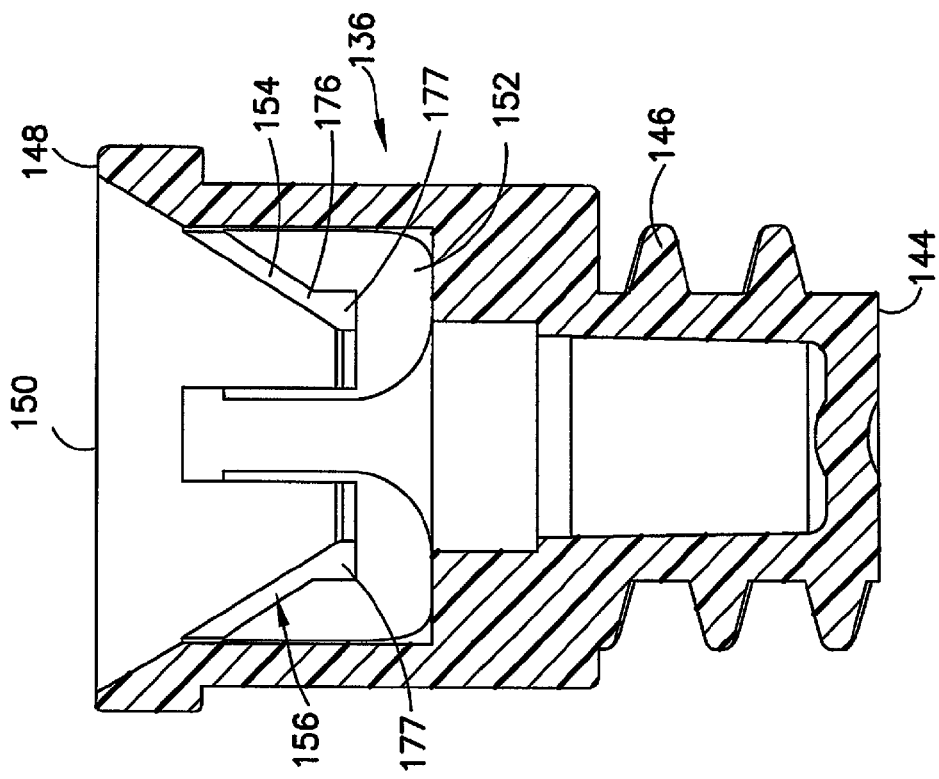
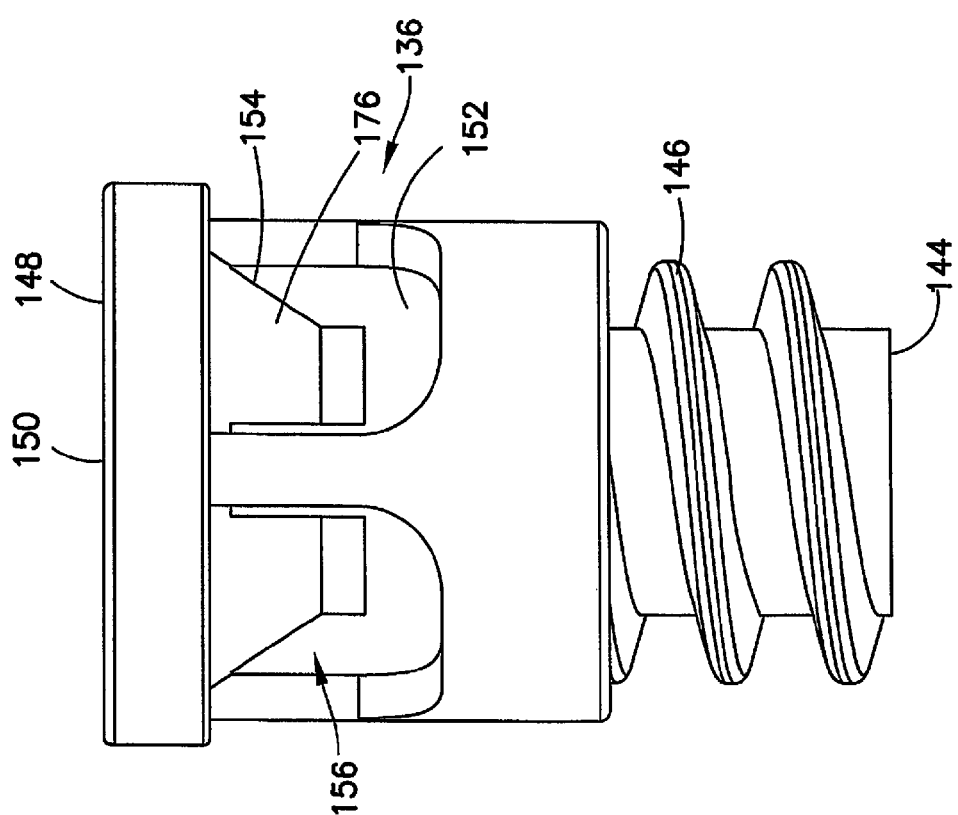

PLUNGER ASSEMBLY INCLUDING A PLUNGER ROD FOR ADVANCING A STOPPER THROUGH A SYRINGE

CROSS-REFERENCE TO RELATED APPLICATION

This application claims priority to U.S. Provisional Application Ser. No. 61/933,058 entitled "Plunger Assembly Including a Plunger Rod for Advancing a Stopper Through a Syringe" filed Jan. 29, 2014, the entire disclosure of which is hereby incorporated by reference.

BACKGROUND OF THE INVENTION

Field of the Disclosure

The present disclosure relates generally to a plunger assembly for use with a syringe adapted for delivery of a fluid. More particularly, the present disclosure relates to a plunger assembly for connecting a plunger rod to a stopper or plunger that can be assembled at the point of use.

Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon the user applying a force to depress the plunger rod and stopper through the syringe barrel towards the front end of the syringe barrel, the contents of the syringe are thereby forced out of the syringe barrel through the opening at the front end for delivery to the patient. Such an operation is well known in the medical field, and medical practitioners have become well accustomed to the use of such common fluid delivery procedures through standard syringes.

Conventional syringes are well known in the medical field to be used in connection with a vial of a medication, where the user collects or draws the fluid into the syringe immediately prior to injection and delivery of the fluid to the patient. Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes may be difficult, since the plunger rod extends beyond the proximal end of the syringe barrel requiring additional space in storage cabinets or automated dispensing cabinets. Therefore, there is a need for a plunger assembly that can be assembled at the point of use, so that the storage volume of the packaged pre-filled syringe is effectively reduced. Specifically, a user should be able to connect the plunger rod to a portion of the syringe just prior to performing a fluid injection. Accordingly, the storage volume of the syringe as a whole has a volume and aspect ratio substantially identical to the syringe barrel. In a storage position, there is no plunger rod extending beyond the proximal end of the syringe barrel. Such a plunger assembly including a plunger rod that can be attached to the syringe at the point of use is disclosed herein.

SUMMARY OF THE INVENTION

According to one aspect of the invention, a plunger assembly is provided herein. The plunger assembly includes a stopper adapter defining an aperture therein. The stopper adapter includes a first restraining member adjacent to the aperture. The plunger assembly also includes a plunger rod having a first end, a second end, and a plunger rod head disposed adjacent the first end of the plunger rod. The plunger rod head includes a second restraining member engageable with the first restraining member of the stopper adapter. The plunger assembly is configured such that as the plunger rod head is moved axially within the aperture of the stopper adapter, the first restraining member of the stopper adapter engages the second restraining member of the plunger rod head to secure the plunger rod head within the aperture.

In another embodiment, a plunger assembly includes a stopper adapter defining an aperture therein. The stopper adapter includes a protruding member adjacent the aperture and a plunger rod having a first end, a second end, and a plunger rod head disposed adjacent the first end of the plunger rod. The plunger rod head includes a deformable restraining member transitionable between a deformed position to an un-deformed position. The plunger assembly is configured such that as the plunger rod head is moved axially within the aperture of the stopper adapter, the protruding member of the stopper adapter deforms the restraining member of the plunger rod head. Once the plunger rod head is advanced beyond the protruding member of the stopper adapter, the restraining member returns to its un-deformed position to secure the plunger rod head within the aperture.

In accordance with another aspect of the invention, a syringe assembly is provided. The syringe assembly includes a syringe barrel having a distal end, an open proximal end, and a sidewall extending therebetween. The syringe assembly also includes a stopper disposed within the syringe barrel having a sidewall with a sliding surface adapted for sealing contact with the sidewall of the syringe barrel and a plunger assembly removeably connected to a proximal end of the stopper for advancing the stopper through the syringe barrel. In this embodiment, the plunger assembly includes a stopper adapter defining an aperture therein. The stopper adapter includes a first restraining member adjacent to the aperture. The plunger assembly also includes a plunger rod having a proximal end, a distal end, and a plunger rod head disposed adjacent the distal end of the plunger rod. In this case, the plunger rod head includes a second restraining member engageable with the first restraining member of the stopper adapter. The plunger assembly is configured such that as the plunger rod head is moved axially within the aperture of the stopper adapter, the first restraining member of the stopper adapter engages the second restraining member of the plunger rod head to secure the plunger rod head within the aperture, such that once the plunger rod head is secured to the adapter, the plunger rod is capable of moving the stopper through the barrel of the syringe in a proximal or a distal direction.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11 is a side view of the syringe adapter of the plunger assembly of FIG. 8.

FIG. 12 is a cross-sectional view of the syringe adapter of FIG. 11.

DETAILED DESCRIPTION

Figure 1A:
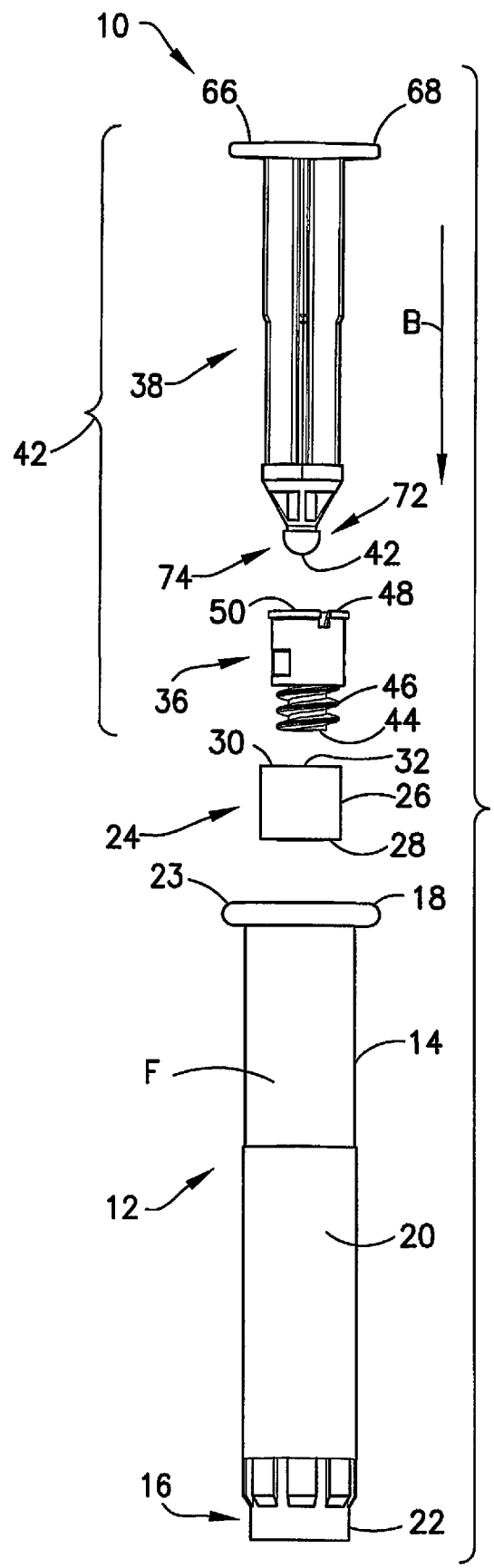
FIG. 1A is an exploded front view of a syringe including a plunger assembly, in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Figure 1B:
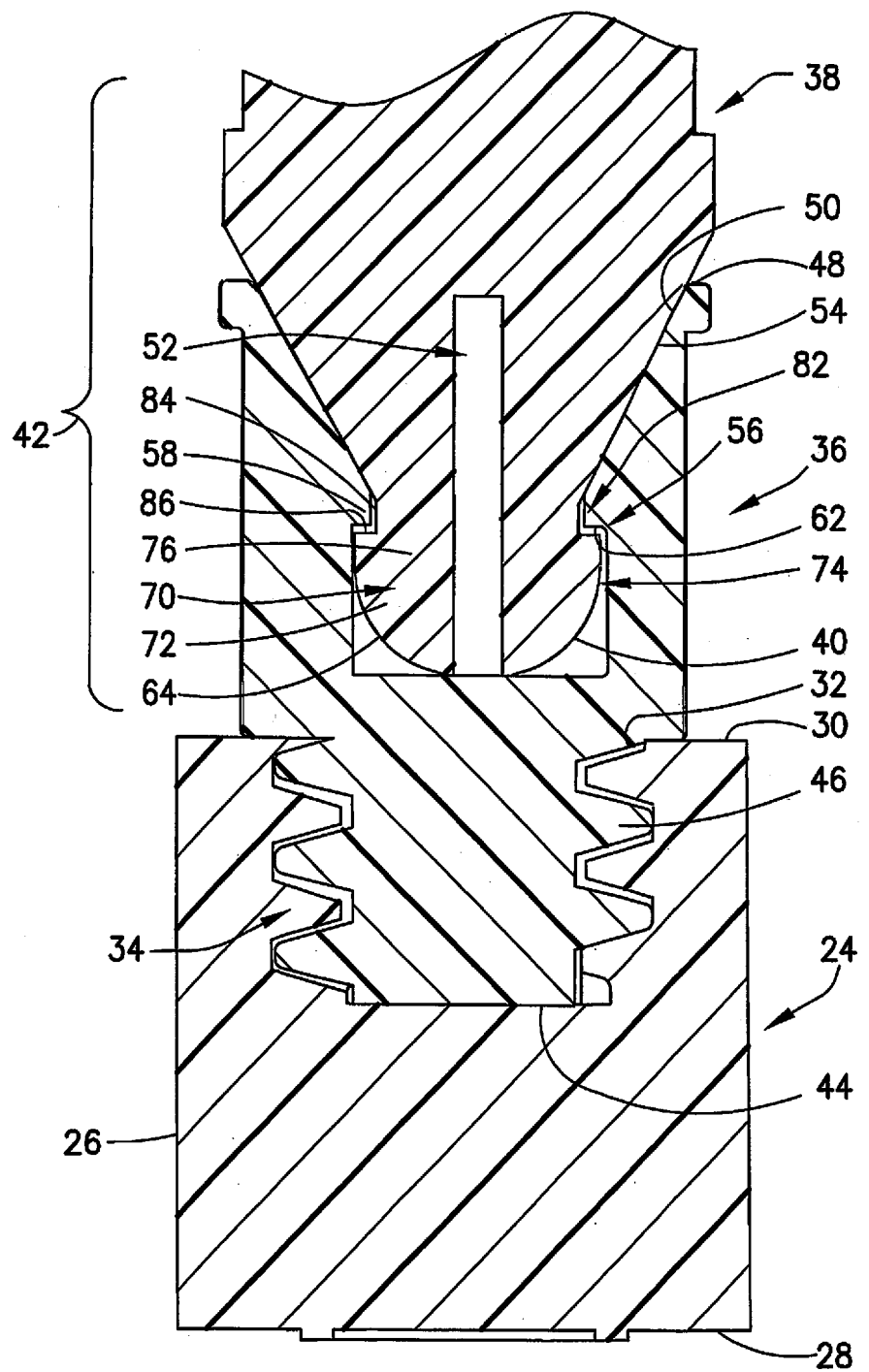
FIG. 1B is a cross-sectional view of a portion of the syringe of FIG. 1A.
Figure 2:
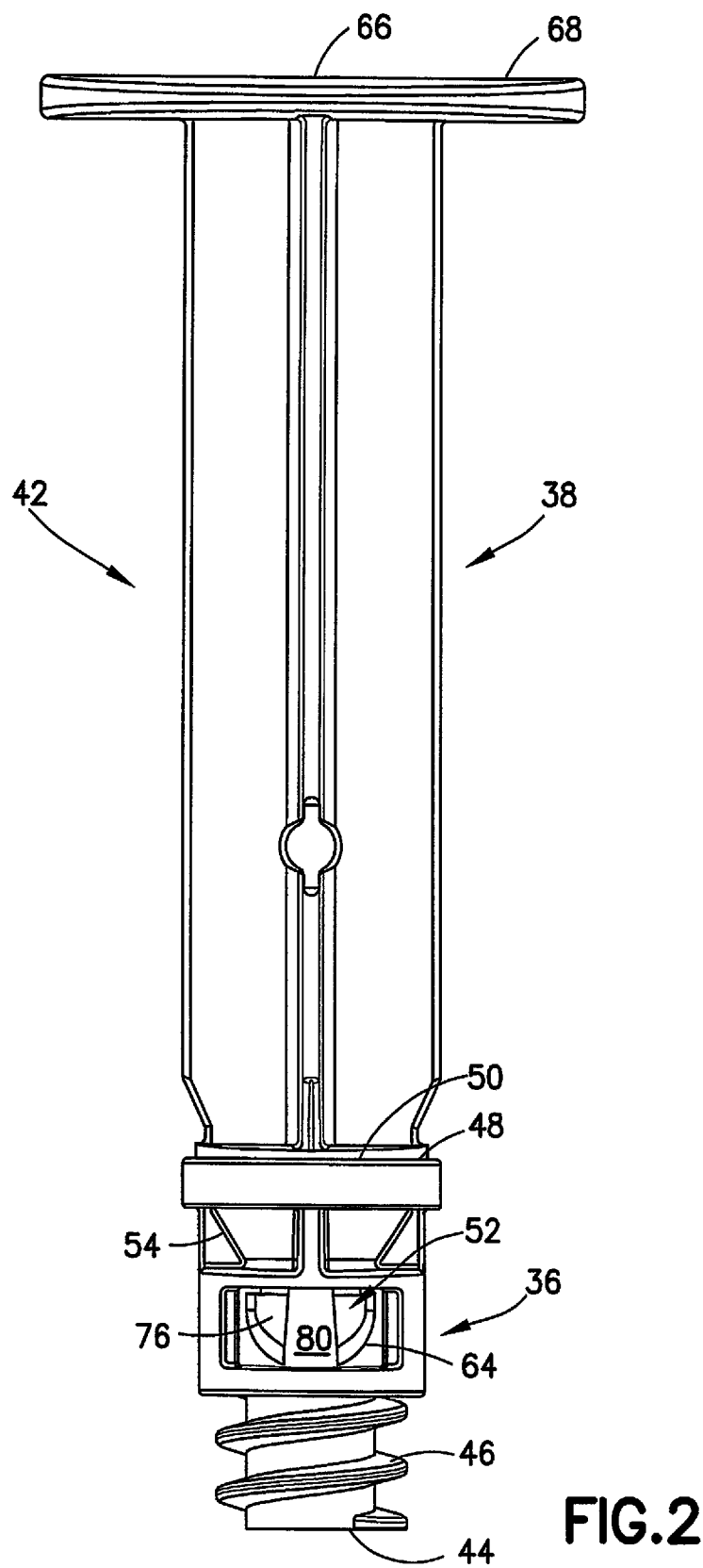
FIG. 2 is a side view of a plunger rod of the plunger assembly of FIG. 1A.

The figures illustrate exemplary embodiments of a plunger assembly for use with a syringe, such as a pre-filled syringe containing a fluid F. Referring to FIGS. 1A and 1B, a syringe 10 including a syringe barrel 12 is illustrated. The syringe barrel 12 generally includes a sidewall 14 extending between a first or distal end 16 and a second or proximal end 18. The sidewall 14 defines an elongate aperture or interior chamber 20 of syringe barrel 12. In one embodiment, the interior chamber 20 spans the extent of syringe barrel 12 so that syringe barrel 12 is cannulated along its entire length. The syringe barrel 12 may be in the general form of an elongated cylindrical barrel as is known in the art in the general shape of a hypodermic syringe. In alternative embodiments, the syringe barrel 12 may be in other forms for containing a fluid for delivery, such as, for example, in the general form of an elongated rectangular barrel. Syringe barrel 12 may be formed of glass, or may be injection molded from thermoplastic material such as polypropylene and polyethylene according to techniques known to those of ordinary skill in the art, though it is to be appreciated that syringe barrel 12 may be made from other suitable materials and according to other applicable techniques, as well.

As is known in the art, the distal end 16 of the syringe barrel 12 may include an outlet opening 22, which is in fluid communication with chamber 20. The outlet opening 22 may be sized and adapted for engagement with a separate device, such as a needle assembly or IV connection assembly and, therefore, may include a mechanism for such engagement, as is conventionally known. For example, the distal end 16 may include a generally-tapered luer tip for engagement with an optional separate tapered luer structure of such a separate device for attachment therewith (not shown).

The proximal end 18 of syringe barrel 12 is generally open-ended, but is intended to be closed off to the external environment. The syringe barrel 12 may also include markings, such as graduations located on sidewall 14, for providing an indication as to the level or amount of fluid F contained within interior chamber 20 of syringe barrel 12. Such markings may be provided on an external surface of sidewall 14, an internal surface of sidewall 14, or integrally formed or otherwise within sidewall 14 of syringe barrel 12. In other embodiments, alternatively, or in addition thereto, the markings may also provide a description of the contents of the syringe or other identifying information as may be known in the art, such as maximum and/or minimum fill lines.

The syringe barrel 12 may be useful as a pre-filled syringe, and, therefore, may be provided for end use with a predetermined volume of fluid F, such as a medication or drug, contained within interior chamber 20 of syringe barrel 12, pre-filled by the manufacturer. In this manner, the syringe barrel 12 can be manufactured, pre-filled with a medication, sterilized, and packaged in appropriate packaging for delivery, storage, and use by the end user, without the need for the end user to fill the syringe with medication from a separate vial prior to use. In such an embodiment, the syringe barrel 12 may include a tip cap (not shown) to seal a fluid F within the interior chamber 20 of syringe barrel 12.

With continued reference to FIG. 1A, a stopper 24 is moveably or slideably disposed within the interior chamber 20 of the syringe barrel 12 and in sealing contact with the internal surface of the sidewall 14 of the syringe barrel 12. The stopper 24 is sized relative to the syringe barrel 12 to provide sealing engagement with the interior surface of sidewall 14 of syringe barrel 12. Additionally, the stopper 24 may include one or more annular ribs 26 extending around the periphery of stopper 24 to increase the sealing engagement between stopper 24 and the interior surface of sidewall 14. In alternate embodiments, a singular O-ring or a plurality of O-rings may be circumferentially disposed about stopper 24 to increase the sealing engagement with the interior surface of sidewall 14 of syringe barrel 12.

With reference to FIGS. 1A and 1B, in one embodiment, the stopper 24 includes a first or distal end 28 and a second or proximal end 30. The proximal end 30 defines a stopper adapter receiving aperture 32 formed therein having a threaded portion 34 for securing the stopper 24 to a corresponding portion of a stopper adapter 36. As will be described in greater detail hereinafter, the stopper adapter 36 connects a plunger rod 38 to the stopper 24. More specifically, the stopper adapter 36 is connected to the stopper 24 by inserting a portion of the adapter 36 into the adapter receiving aperture 32 of the stopper 24. A user then moves the plunger rod 38 in a distal direction signified by arrow B in FIG. 1A, causing a distal end 40 of the plunger rod 38 to contact and form a removable or non-removable engagement between the plunger rod 38 and the stopper adapter 36. Since the stopper adapter 36 is connected to the stopper 24, continued movement of the plunger rod 38 in the distal direction advances the stopper 24 through the syringe barrel 12, for expelling fluid F therefrom. For convenience, the plunger rod 38 and stopper adapter 36 are collectively referred to hereinafter as a plunger assembly 42.

By having the plunger assembly 42 separate and detached from the stopper 24 and syringe barrel 12, the plunger assembly 42 can be separately placed in product-packaging, stored, and shipped, even when the syringe barrel 12 is pre-filled with a fluid F (shown in FIG. 1A). In contrast, a conventional pre-filled syringe is typically packaged with a plunger rod retracted out of a back or proximal end of a syringe barrel. Accordingly, packaging of such pre-filled syringes is bulky and awkward for shipping and storage. For example, the overall length to be packaged of a conventional pre-filled syringe is equal to the length of the syringe barrel and the length that the plunger rod extends outwardly from the syringe barrel. Accordingly, a syringe in accordance with the present invention allows plunger rod 38 and syringe barrel 12 to be packaged in a manner that allows for reduced storage space. Advantageously, a pre-filled syringe, shipped without an attached plunger rod, fits easily in an automated dispensing cabinet. Accordingly, the syringe 10 disclosed herein can be easily used in modern pharmacies and medical facilities with specific space requirements. Additionally, the syringe 10 disclosed herein is configured so that upon removal of plunger rod 38 and syringe barrel 12 from a storage facility, automated dispensing cabinet, and/or product packaging elements, the plunger rod 38 can quickly and easily be secured to the syringe barrel 12 for collecting a fluid and/or delivering a fluid.

Having generally described the syringe 10 and stopper 24, the structure of various embodiments of the plunger assembly 42 will now be described in detail. With reference to FIGS. 1B-6, a non-limiting embodiment of the plunger assembly 42 is illustrated. The plunger assembly 42 includes the stopper adapter 36 and the plunger rod 38. A distal end 44 of the stopper adapter 36 includes a threaded portion 46 configured for insertion in the adapter receiving aperture 32 of the stopper 24 and for connection to the threaded portion 34 of the stopper 24 as shown, for example, in FIGS. 1A and 1B. In other embodiments, the stopper adapter 36 is secured to the stopper 24 using a ball detent, locking tabs, spring loaded locking mechanism, latch, adhesive, or other similar mechanism. The stopper adapter 36 is locked, secured, or engaged to stopper 24, i.e., significant relative movement between stopper adapter 36 and stopper 24 is prevented. In other alternate embodiments, the stopper adapter 36 and the stopper 24 may be integrally formed. In a further alternative embodiment, the adapter 36 and stopper 24 may be co-formed such as by co-extrusion or two-shot molding. In a further alternate embodiment, the stopper adapter 36 and stopper 24 may be integrally formed together to form a single stopper assembly.

With continued reference to FIGS. 1B-6, a second or proximal end 48 of the stopper adapter 36 includes a plunger receiving aperture 50 formed therein. The aperture 50 is adjacent a cavity 52 extending into an interior of the adapter 36. In certain embodiments, the cavity 52 is a substantially conical cavity including a sloped sidewall that forms a conical mating surface 54. A securement feature or engagement portion, referred to hereinafter as a first restraining member 56, extends into a portion of the cavity 52 for securing the plunger rod 38 to the stopper adapter 36. In one embodiment, the first restraining member 56 includes a protruding annular ring 58 having a tapered portion and a locking end 62. The protruding annular ring 58 may be formed of a rigid, unyielding material.

The plunger rod 38 of the plunger assembly 42 is adapted for advancing the stopper 24 through the syringe barrel (shown in FIGS. 1A and 1B). Thus, with continued reference to FIGS. 1B-6, the plunger rod 38 may be sized for movement within interior chamber 20 of syringe barrel 12, and generally includes a first or distal end 64, a second or proximal end 66, and a flange 68 disposed adjacent to the proximal end 66. The flange 68 is a thumb press adapted so that a user can press against the flange 68 with his or her thumb. Accordingly, the flange 68 may include a thumb-shaped depression (not shown), as well as various textured portions to prevent the thumb from slipping from the flange 68. The plunger rod 38 further includes a securement feature or engagement portion 70 for securing the plunger rod 38 to the adapter 36. In one embodiment, a plunger rod head 72 has a deformable restraining member 74, such as elastic fingers 76 and a neck 78 disposed adjacent plunger rod head 72. The fingers 76 are separated by a slot 80 extending from the neck 78 to the distal end 40 of the plunger rod 38. The plunger rod head 72 also includes an annular groove 82 located between elastic fingers 76 and neck 78. The elastic fingers 76 each include a tapered portion 84 and a locking end 86.

Figure 4:
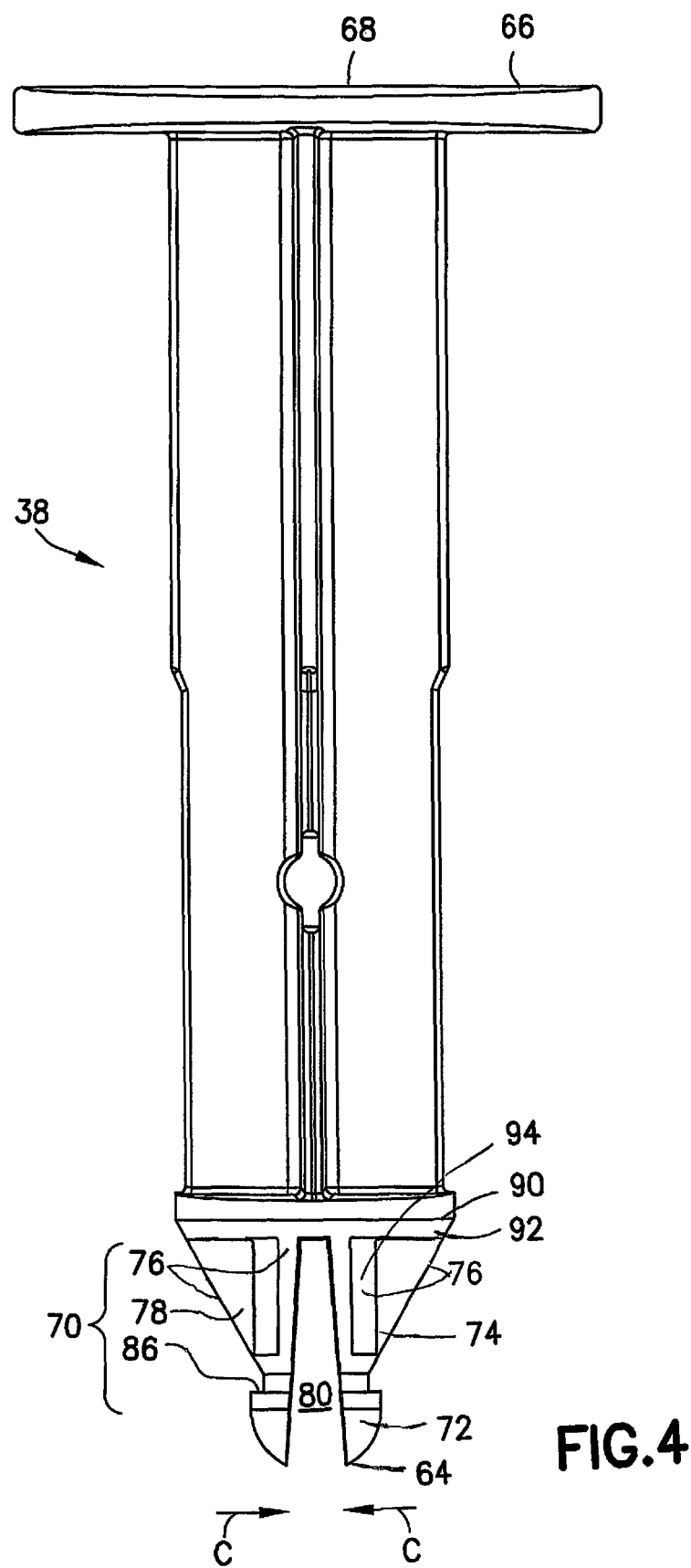
FIG. 4 is a side view of a plunger rod of the plunger assembly of FIG. 1A.
Figure 4A:
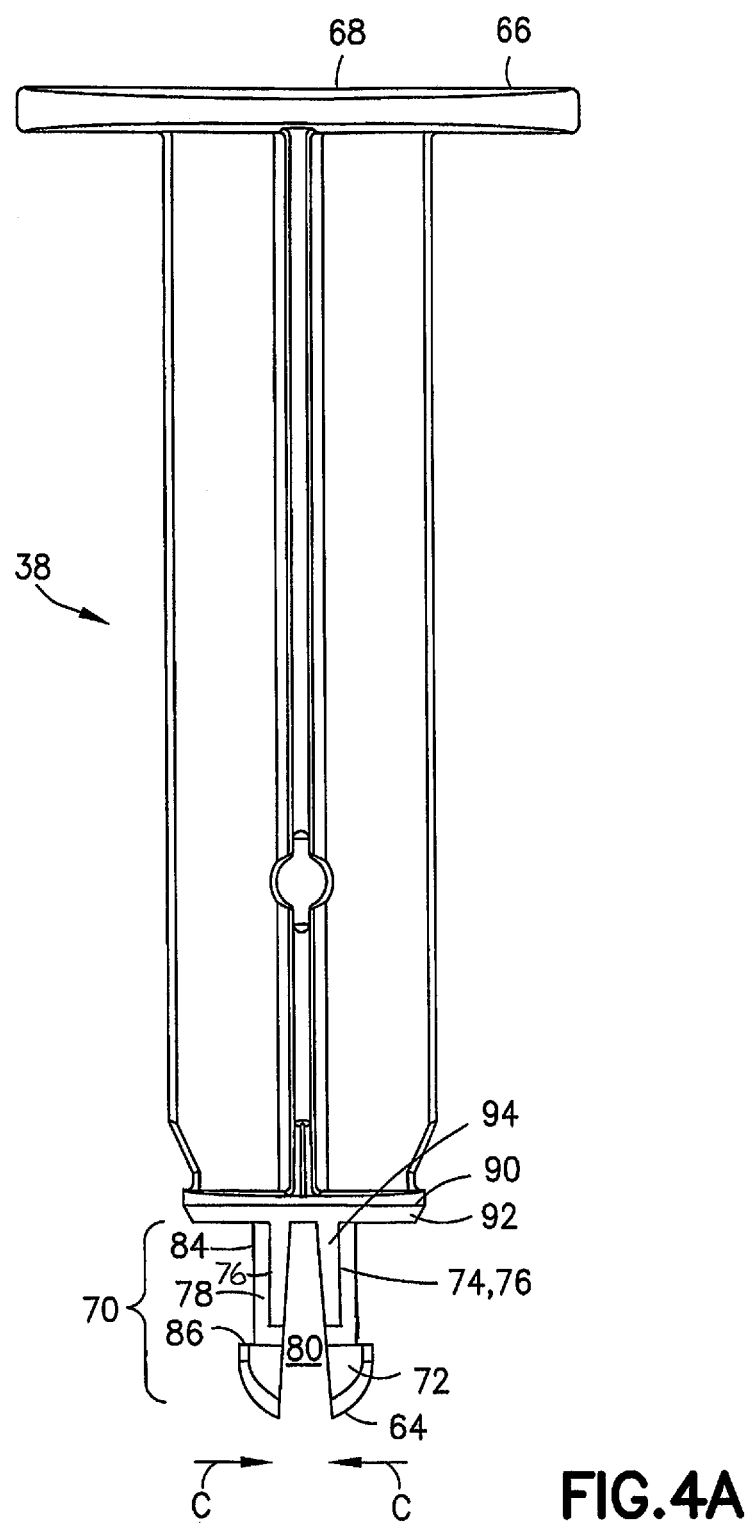
FIG. 4A is an alternative side view of a plunger rod of the plunger assembly having an alternative deformable restraining member including a different arrangement of elastic fingers.
Figure 6:
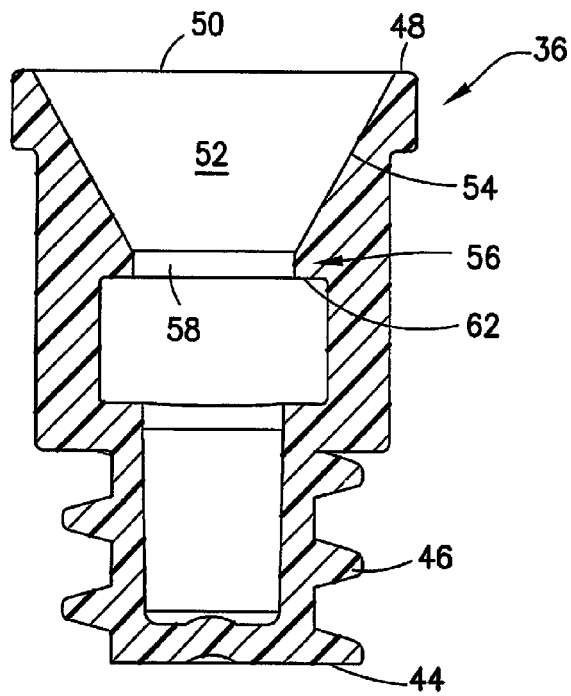
FIG. 6 is a cross-sectional view of the syringe adapter of FIG. 5.
Figure 5:
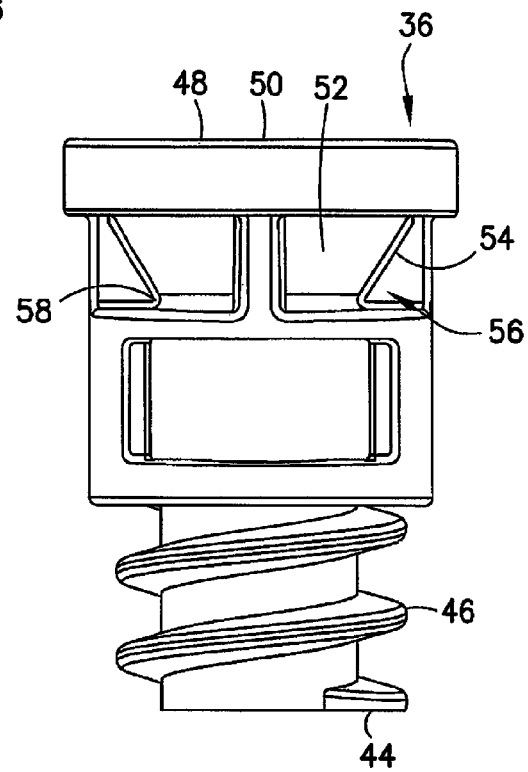
FIG. 5 is side view of a syringe adapter of the plunger assembly of FIG. 1A.

With reference to FIGS. 4 and 4A specifically, it is noted that the deformable restraining member 74 may include a plurality of elastic fingers 76 provided about the plunger rod head 72. For example, as shown in FIG. 4, four elastic fingers 76 may be evenly spaced about the plunger rod 38. In this configuration, slot 80 may bisect two of the opposed elastic fingers 76, such as to create the appearance of six elastic fingers. Alternatively, as shown in FIG. 4A, two elastic fingers 76 may be evenly disposed about the plunger rod 38. In this configuration, slot 80 may bisect two of the opposed elastic fingers, such as to create the appearance of four elastic fingers. It is also contemplated herein that other configurations of elastic fingers 76 may be provided about the plunger rod 38, provided more than one elastic finger 76 is incorporated in the plunger rod 38. For example, three or six elastic fingers may also be provided in an evenly distributed position about the plunger rod 38 provided they perform the functionality as described herein.

Figure 7:
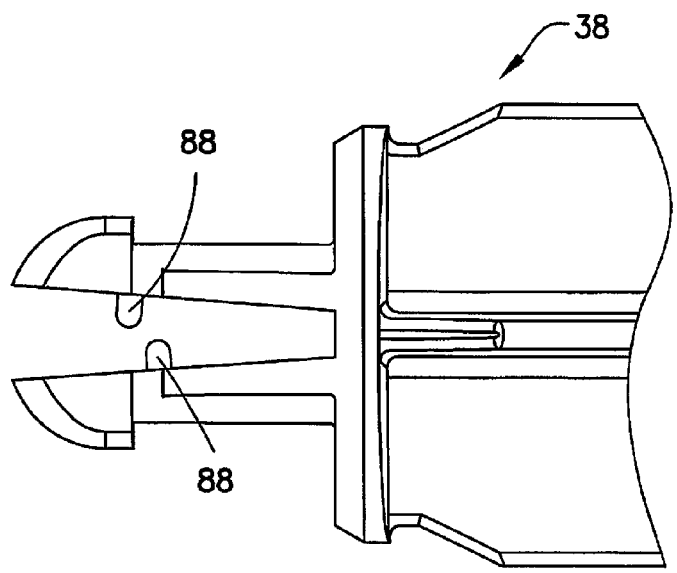
FIG. 7 is a side view of a portion of a plunger rod, in accordance with a further embodiment of the invention.

With reference to FIG. 7, in certain embodiments, the plunger rod 38 includes anti-nesting features 88 for preventing two plunger rods from becoming stuck together or attached to one another during shipping, transport, or packaging of the plunger assembly 42. For example, one or more anti-nesting ribs 88 may extend from an inner surface of the elastic fingers 76 into the slot 80 of the plunger rod head 72. The anti-nesting ribs 88 prevent an elastic finger of another plunger rod from becoming tangled or inserted in the slit of the plunger rod. As such, it is less likely that the plunger rod or elastic fingers will break during shipping.

With reference to FIGS. 1B-7, the plunger rod head 72 also includes features for enhancing the stability of the plunger rod 38 relative to the stopper adapter 36, when secured thereto. For example, in one preferred and non-limiting embodiment, the plunger rod head 72 includes a flange 90 having a chamfered boss 92 sized and adapted to contact a portion of the conical mating surface 54 of the cavity 52. When the plunger rod 38 is secured to the adapter 36, the chamfered boss 92 restricts radial movement of the plunger rod 38, thereby enhancing the stability of the connection between the adapter 36 and rod 38. The plunger rod head 72 may also include one or more angled ribs 94 extending from the chamfered boss 92 toward the distal end 40 of the plunger rod 38. The angled ribs 94 generally have a slope that corresponds to the slope of the conical mating surface 54 of the adapter 36. When the plunger rod head 72 is secured to the adapter 36, the angled ribs 94 contact the conical mating surface 54 to restrict radial movement of the plunger rod 38.

In addition to improving stability of the connection between the plunger rod 38 and adapter 36, the combination of the conical cavity 52 and plunger rod head 72 also serves as a visual cue that assists the user to insert the plunger rod 38 into the adapter 36 in the correct axial and radial orientation. Specifically, the conical shape of the cavity 52 helps a user to visualize correct placement of the plunger within the cavity, by providing a target, formed by the distal end of the conical cavity 52. The user need only aim the plunger rod head 72 at the center of the cavity 52 to ensure good alignment between the plunger rod 38 and adapter 36. Once the plunger rod head 72 is in the cavity 52, the chamfered boss 92 and angled ribs 94 provide additional assistance and support in correctly aligning the plunger rod 38 to the adapter 36.

With continued reference to FIGS. 1B-7, a method of securing the-plunger rod 38 to the stopper adapter 36 and for advancing the stopper adapter 36 and stopper 24 through the syringe barrel 12 will now be described. Specifically, with the plunger rod head 72 of the plunger rod 38 positioned adjacent to the plunger receiving aperture 50 of the stopper adapter 36, the plunger rod 38 is inserted or moved axially into plunger receiving aperture 50 in a direction generally along arrow B shown in FIG. 1A, such that elastic fingers 76 of plunger rod head 72 are disposed within plunger receiving aperture 50 of stopper adapter 36.

Figure 3:
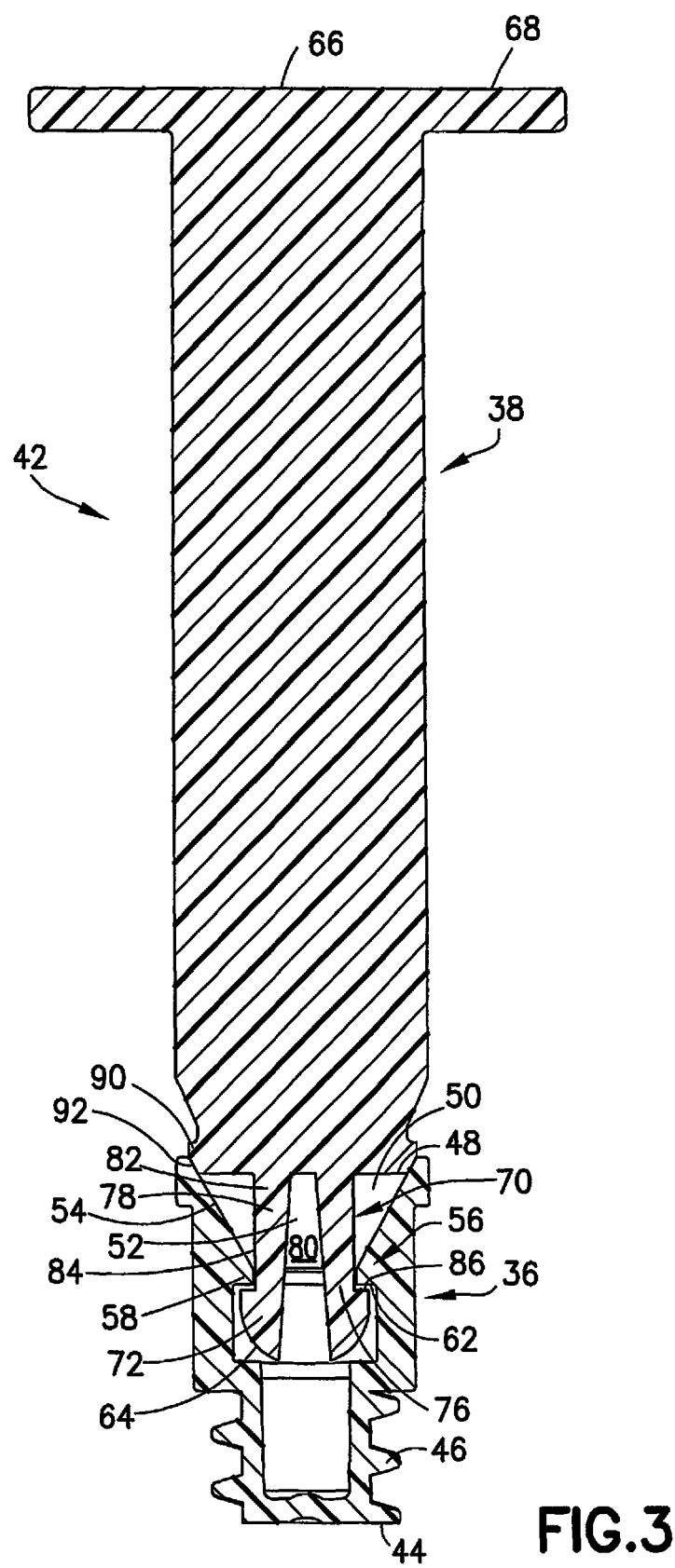
FIG. 3 is a cross sectional view of the plunger assembly of FIG. 2.

As additional force is exerted on plunger rod 38 to axially move plunger rod head 72 in the direction generally along arrow B, the elastic fingers 76 cooperate with the tapered portion 84 of protruding annular ring 58 and the protruding annular ring 58 pushes or compresses the elastic fingers 76 in a direction generally along arrow C (FIG. 4) until the elastic fingers 76 of the plunger rod head 72 slide over and past the tapered portion 84 of the protruding annular ring 58 and lock the plunger rod head 72 to the stopper adapter 36. Once the elastic fingers 76 slide over and past a tapered portion of the protruding annular ring 58, the elastic fingers 76 return to their original position as shown in FIG. 3. In this position, referring to FIG. 3, the locking end 62 of the protruding annular ring 58 abuts, contacts, or engages the locking end 86 of the elastic fingers 76 with the protruding annular ring 58 disposed adjacent the annular groove 82 of the plunger rod head 72 and locks or secures the plunger rod 38 to the stopper adapter 36. This configuration ensures that with the elastic fingers 76 mechanically locked over the protruding annular ring 58, the plunger rod 38 is secured to the stopper adapter 36, such that significant relative movement between the plunger rod 38 and the stopper adapter 36 is prevented. In this manner, the plunger rod 38 is adapted for advancing the stopper 24 within syringe barrel 12 (shown in FIG. 1A).

With reference to FIG. 1A, once the plunger rod 38 is secured to the stopper 24, a user can remove a sealing cap member (not shown) from distal end 16 of syringe barrel 12 and can attach the distal end 16 to a separate needle assembly or IV connection assembly in any known manner. Prior to dispensing any medication, any air trapped within chamber 20 of syringe barrel 12 can be expelled in a known manner.

When it is desired to expel or deliver the medication contained within the syringe barrel 12, the syringe is grasped with the user's thumb on the flange 68 of the plunger rod 38 and with the user's fingers grasping and extending around a flange 23 of syringe barrel 12. In this manner, the syringe 10 is grasped by a user in a well-known and well recognized manner similar to the operation of a conventional hypodermic syringe. Next, the user effects a squeezing movement between the thumb on the flange 68 and fingers on the grasping flange 23 of the syringe barrel 12, thereby causing the flange 68 of plunger rod 38 to move in a distal direction toward the proximal end 18 of the syringe barrel 12. In this manner, movement of stopper 24 in the distal direction forces the fluid F contained within chamber 20 of syringe barrel 12 to be forced out of the outlet opening 22 of syringe barrel 12 to deliver the fluid F to a patient.

Having described a preferred and non-limiting embodiment of a plunger assembly and a method of use thereof, alternative preferred and non-limiting embodiments of plunger assemblies will now be discussed in detail.

With reference to FIGS. 8-12, in a further preferred and non-limiting embodiment, a plunger assembly 142 includes a plunger rod 138 and a stopper adapter 136. As in the previously described embodiment, the adapter 136 includes a distal end 144 having a threaded portion 146 configured for insertion in an adapter receiving aperture (shown in FIG. 1A) of a stopper and for connection to a threaded portion of the stopper. In other embodiments, the stopper adapter 136 is secured to the stopper using a ball detent, locking tabs, spring loaded locking mechanism, latch, adhesive, or other similar mechanism. The stopper adapter 136 is locked, secured, or engaged to stopper, i.e., significant relative movement between stopper adapter 136 and the stopper is prevented.

Figure 8:
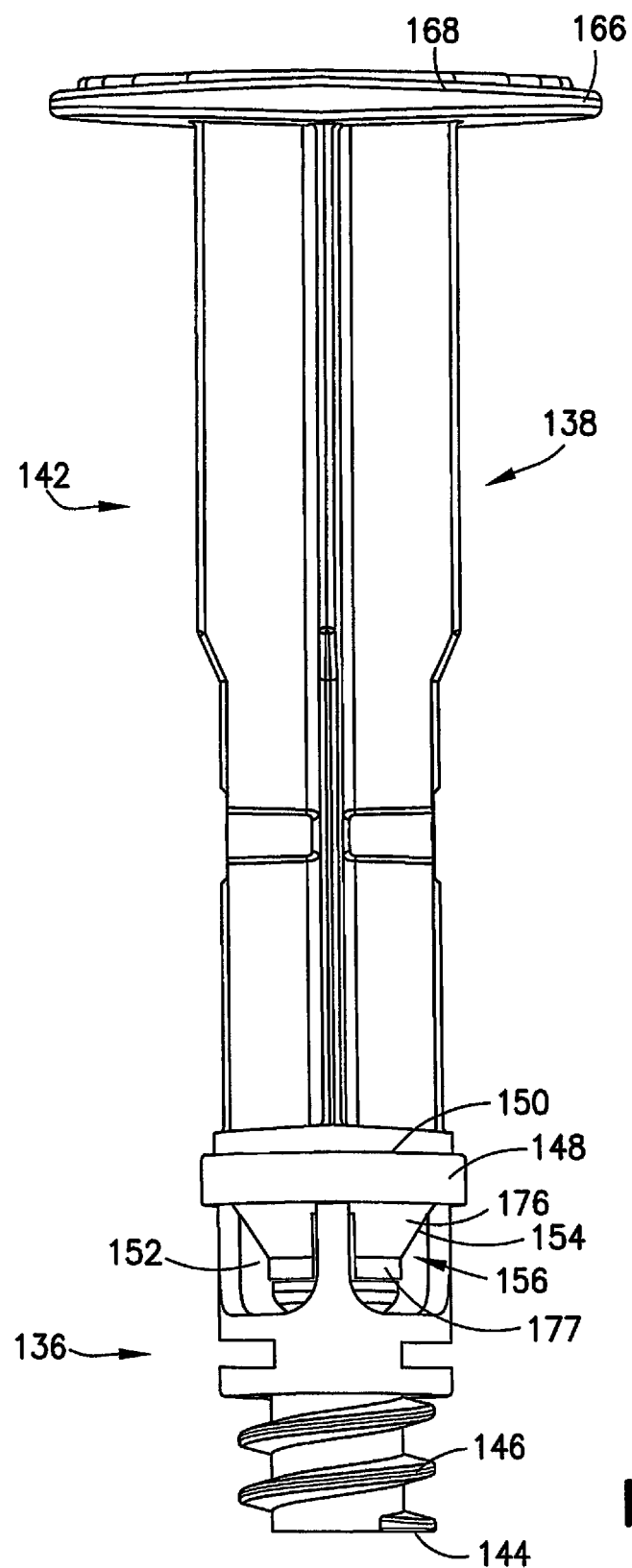
FIG. 8 is a side view of a plunger assembly, in accordance with a further embodiment of the invention.
Figure 9:
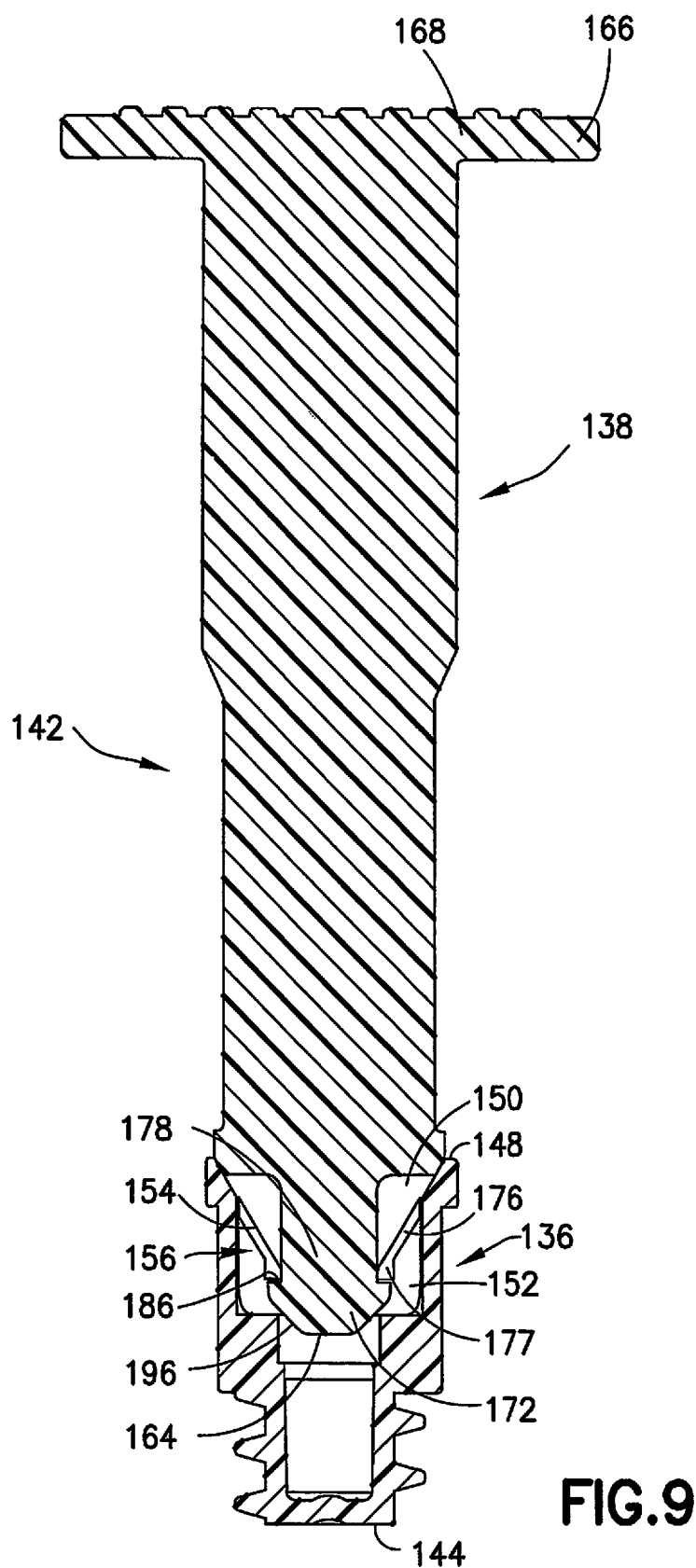
FIG. 9 is a cross-sectional view of the plunger assembly of FIG. 8.
Figure 10:
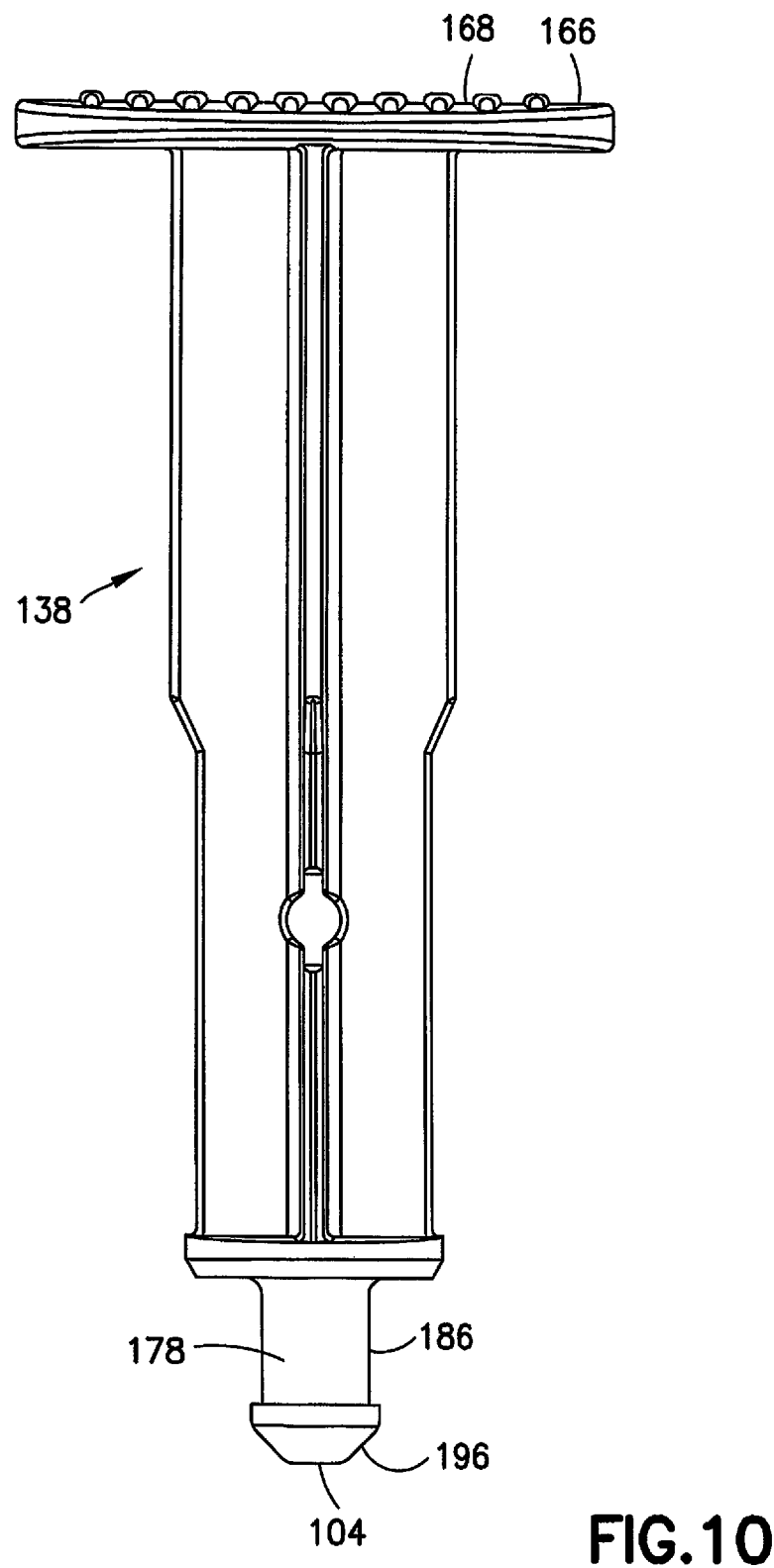
FIG. 10 is a side view of a plunger rod of the plunger assembly of FIG. 8.
Figure 13:
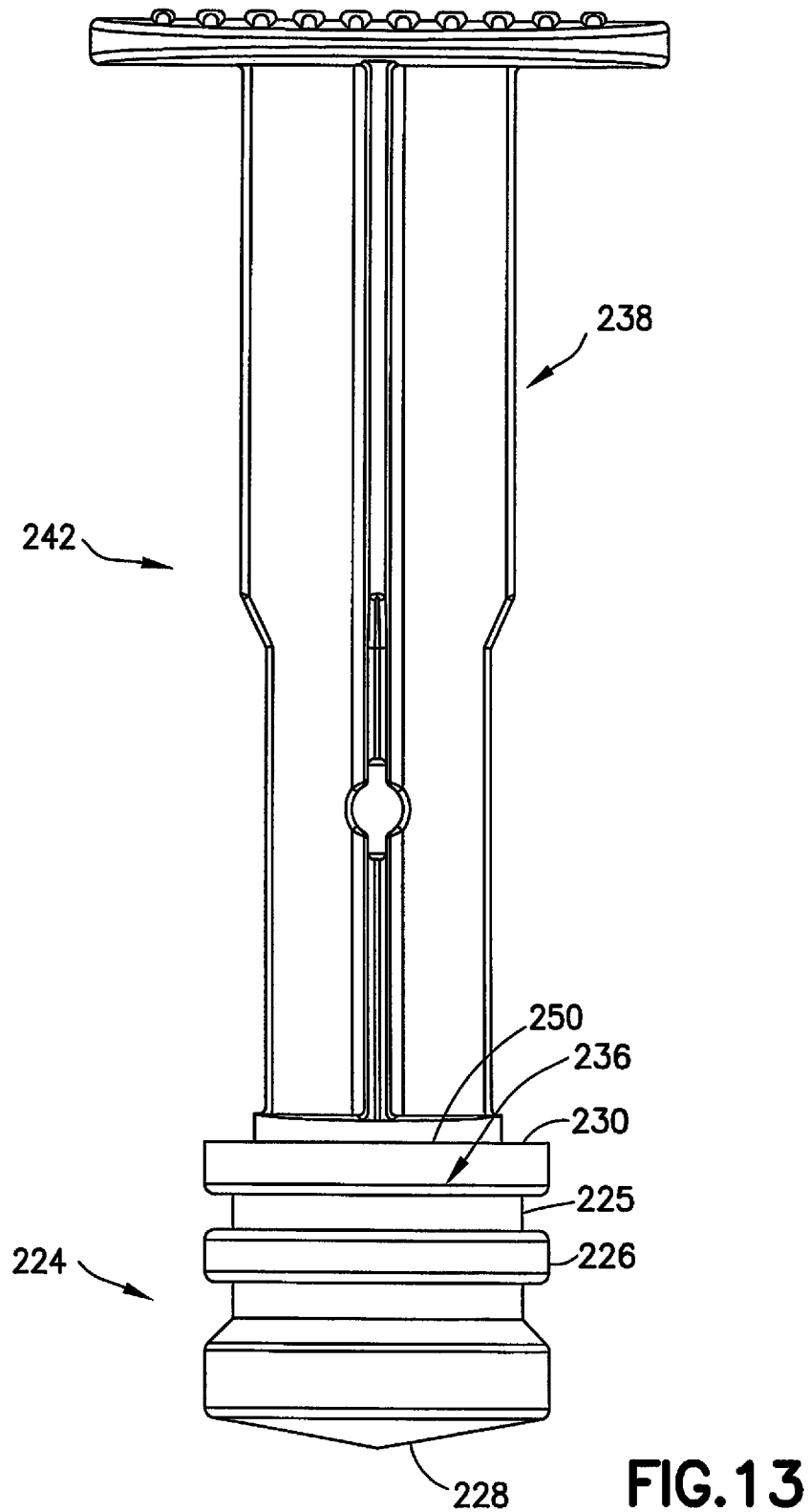
FIG. 13 is a side view of a plunger assembly, in accordance with a further embodiment of the invention.

With continued reference to FIGS. 8-12, a second or proximal end 148 of the stopper adapter 136 includes a plunger receiving aperture 150 formed therein. The aperture 150 is adjacent a cavity 152 of the adapter 136. A securement feature or engagement portion, referred to hereinafter as a first restraining member 156, extends into a portion of the cavity 152 for securing the plunger rod 138 to the stopper adapter 136. In contrast to previously described embodiments, the first restraining member 156 of the plunger assembly 142 illustrated in FIGS. 5 and 6 has a deformable structure, such as one or more elastic fingers 176 extending into the cavity 152. The elastic fingers 176 may be positioned in a conical orientation, as shown in FIG. 8. Specifically, the elastic fingers 176 may extend from the proximal end 148 of the adapter 136, adjacent the plunger receiving aperture 150, toward the interior of the cavity 152. In this arrangement, distal ends 177 of the fingers 176 are generally closer together than the proximal ends of the fingers 176, thereby forming the conical arrangement. Application of force against the fingers 176 causes the fingers 176 to depress, such that the distal ends 177 of the fingers 176 move radially outward from the center of the cavity 152.

As in previously described embodiments, the plunger rod 138 of the plunger assembly 142 is adapted for advancing the stopper 24 through the syringe barrel 12 (shown in FIGS. 1A and 1B). The plunger rod 138 includes a securement feature or engagement portion, referred to hereinafter as a restraining member, for securing the plunger rod 138 to the adapter 136. In one embodiment, the restraining member includes a plunger rod head 172 and a neck 178 disposed adjacent the plunger rod head 172. The plunger rod head 172 includes a sloped surface 196 that corresponds to the angle of the elastic fingers 176 of the stopper adapter 136. The head 172 also includes a locking end 186 or shelf on a proximal end thereof for contacting the distal ends 177 of the elastic fingers 176 of the adapter 136.

With continued reference to FIGS. 8-12, steps for securing the plunger rod 138 to the stopper adapter 136 are now described. Specifically, with the plunger rod head 172 of the plunger rod 138 positioned adjacent to the plunger receiving aperture 150 of the stopper adapter 136, the plunger rod 138 is inserted or moved axially into plunger receiving aperture 150, such that the head is disposed within the plunger receiving aperture 150 of the adapter 136. The sloped surface 196 of the head 172 is adjacent to the elastic fingers 176 of the adapter 136. As additional force is exerted on plunger rod 138 to axially move plunger rod head 172 within the plunger receiving aperture 150, the sloped surface 196 presses against the elastic fingers 176 compressing the elastic fingers 176 and causing the fingers 176 to move radially outward from the center of the cavity 152. Once the head 172 passes the distal end 177 of the elastic fingers 176, the fingers 176 return to their original position within the cavity 152 of the adapter 136. In this position, the distal ends 177 of the fingers 176 contact the locking end 186 of the head 172 effectively maintaining the head 172 within the cavity 152 and preventing movement of the plunger rod 138 in the proximal direction.

With reference to FIGS. 13-16, a further preferred and non-limiting embodiment of a plunger assembly 242 is illustrated. The assembly 242 includes a stopper 224 with an integral stopper adapter 236 and a separate plunger rod 238. The stopper 224 is formed from a suitable flexible elastomeric material, such as a synthetic polymer or natural rubber. The stopper 224 includes a conical distal end 228 for contacting fluid contained within the syringe barrel, a proximal end 230 having a plunger receiving aperture 250 formed therein, and a substantially cylindrical sidewall 225 extending therebetween. The sidewall 225 may include one or more ribs 226 extending therefrom. The ribs 226 have a diameter which corresponds to or is slightly larger than the diameter of the syringe barrel (shown in FIG. 1A), such that a sealing engagement between the ribs 226 and the interior surface of the syringe barrel is formed when the stopper 224 is inserted in the syringe barrel.

Figure 14:
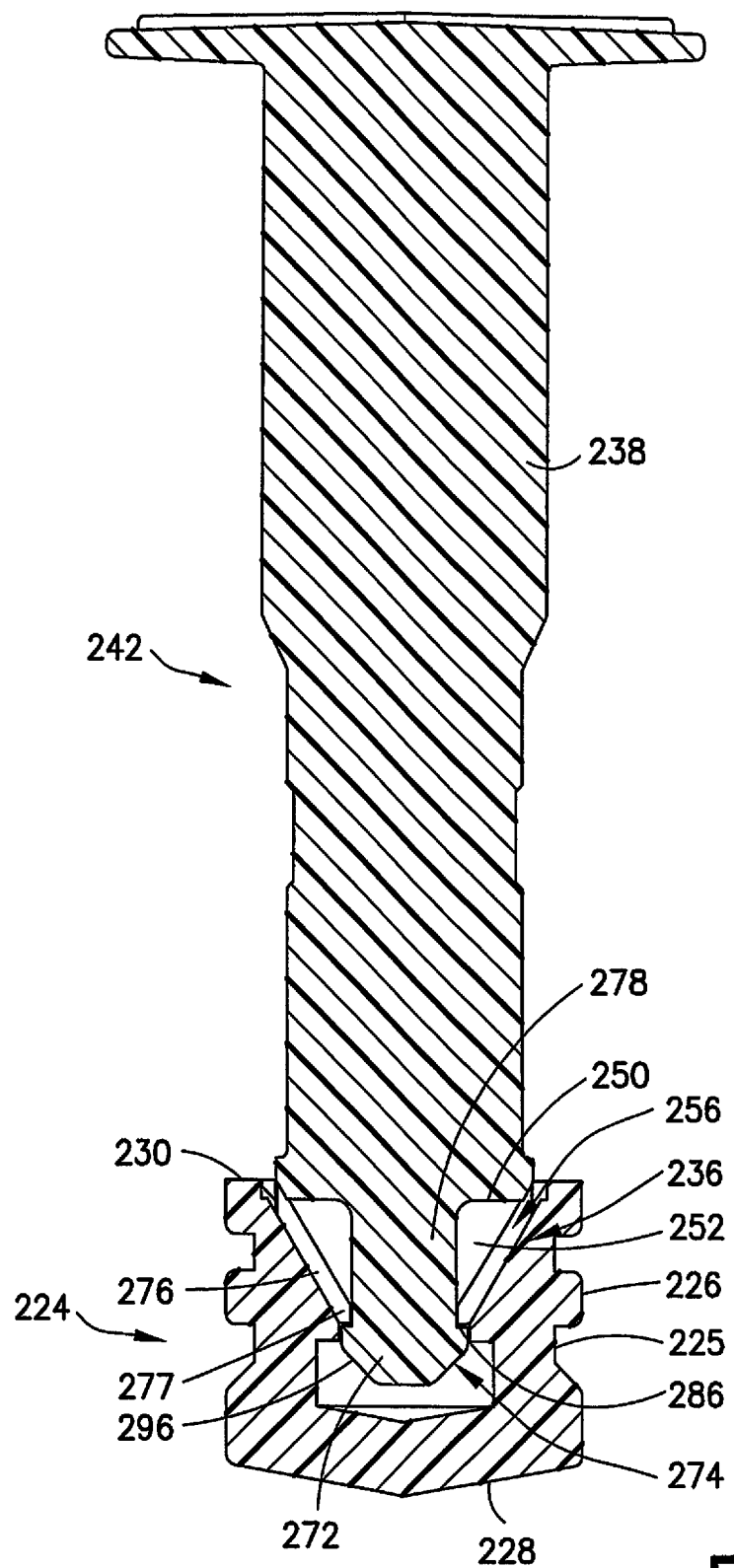
FIG. 14 is a cross-sectional view of the plunger assembly of FIG. 13.
Figure 15:
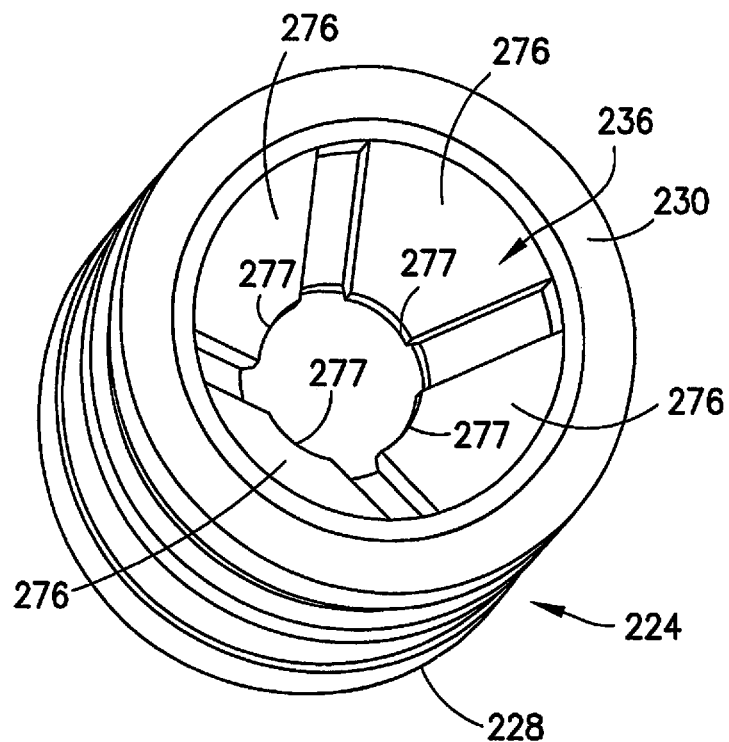
FIG. 15 is a perspective view of the stopper adapter and stopper of the plunger assembly of FIG. 14.
Figure 16:
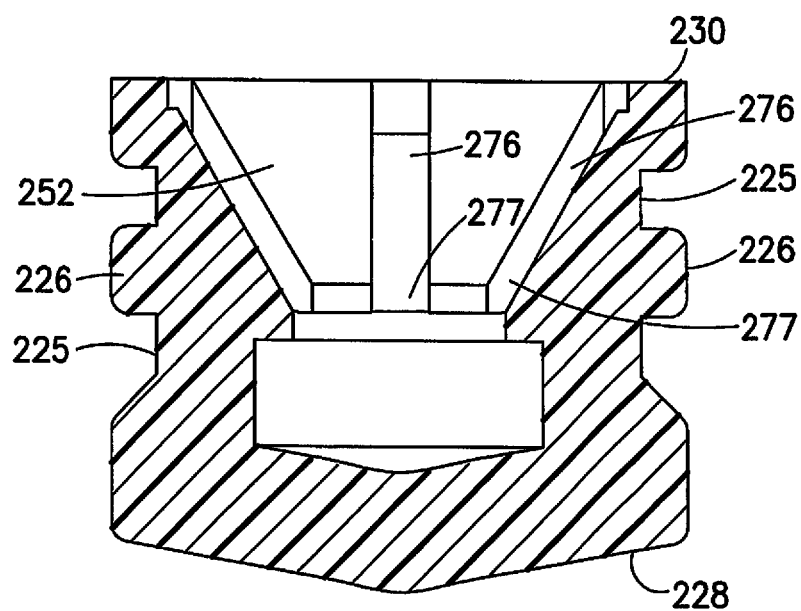
FIG. 16 is a cross-sectional view of the stopper adapter and stopper of FIG. 15.

With continued reference to FIGS. 13-16, a conical cavity 252 (shown in FIGS. 14-16) is formed within the interior of the stopper 224 adjacent to the plunger receiving aperture 250. In the embodiment of FIGS. 13-16, the stopper adapter 236 is positioned within the cavity 252. With reference to FIGS. 14-16, the adapter 236 includes a securement feature or engagement portion, referred to hereinafter as a first restraining member 256, extending into a portion of the cavity 252 for securing the plunger rod 238 to the stopper adapter 236. The first restraining member 256 has a deformable structure, such as one or more elastic fingers 276 extending into the cavity 252. The elastic fingers 276 may be positioned in a conical orientation, as shown in FIG. 14 and FIG. 15. Specifically, the elastic fingers 276 may extend from the proximal end 230 of the stopper 224, adjacent the plunger receiving aperture 250, toward the interior of the cavity 252. Distal ends 277 of the fingers 276 may be closer together than the proximal ends of the fingers 276 to form the conical arrangement. Application of force against the fingers 276 causes the distal end 277 of the fingers 276, as well as the stopper 224 itself, to depress radially outward from the center of the cavity 252. As will be appreciated by one having ordinary skill in the art, the stopper 224 and adapter 236 may be formed separately and connected together using any known fastening or adhesive means. Alternatively, the stopper 224 and adapter 236 may be formed together at the same time, such as by a two-shot molding process that incorporates the stopper 224 into the adapter 236.

The plunger rod 238 of the plunger assembly 242 is identical to the plunger rod 138 depicted in FIGS. 8-12 described above. Specifically, the plunger rod 238 includes a securement feature or engagement portion, referred to hereinafter as a second restraining member 274, for securing the plunger rod 238 to the adapter 236. In one embodiment, the second restraining member 274 includes a plunger rod head 272 and a neck 278 disposed adjacent the plunger rod head 272. The plunger rod head 272 includes a sloped surface 296 that corresponds to the angle of the elastic fingers 276 of the stopper adapter 236. The head 272 also includes a locking end 286 or shelf on a proximal end thereof for contacting the distal ends 277 of the elastic fingers 276 of the adapter 236.

With continued reference to FIGS. 13-16, steps for securing the plunger rod 238 to the stopper adapter 236 are described. Specifically, with the plunger rod head 272 of the plunger rod 238 positioned adjacent to the plunger receiving aperture 250 of the stopper adapter 236, the plunger rod 238 is inserted or moved axially into plunger receiving aperture 250, such that the head 272 is disposed within the plunger receiving aperture 250 of the adapter 236. In this position, the sloped surface 296 of the head 272 is adjacent to the elastic fingers 276 of the adapter 236. As additional force is exerted on plunger rod 238, the sloped surface 296 presses against the elastic fingers 276 depressing the elastic fingers 276 and causing them to move radially outward from the center of the cavity 252. The fingers 276 are adjacent to the interior surface of the cavity 252 of the stopper 224. Thus, pressing against the fingers 276 also causes the stopper 224 to deform, thereby increasing the size of the cavity 252. The increase in the size of the cavity 252 allows the plunger head 272 to advance through the cavity 252 up to and beyond the distal ends 277 of the fingers 276. Once the head passes the distal end 277 of the elastic fingers 276, the fingers 276 and stopper 224 return to their original positions. In this position, the distal ends 277 of the fingers 276 contact the locking end of the head 272 effectively maintaining the head 272 within the cavity and preventing movement of the plunger rod 238 in the proximal direction.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A plunger assembly comprising:
    a stopper adapter comprising a sloped sidewall, which defines an aperture and a cavity having a conical mating surface, and a first restraining member adjacent to the aperture; and
    a plunger rod comprising:
        a first end,
        a second end,
        a plunger rod head disposed adjacent the first end of the plunger rod, the plunger rod head comprising a second restraining member engageable with the first restraining member of the stopper adapter, and
        an annular flange proximal to the second restraining member having a radially outer surface configured to contact a portion of the conical mating surface of the stopper adapter to restrict radial movement of the plunger rod relative to the stopper adapter when the plunger rod head is secured within the aperture,
    wherein as the plunger rod head is moved axially within the cavity of the stopper adapter, the first restraining member of the stopper adapter engages the second restraining member of the plunger rod head to secure the plunger rod head within the cavity.

2. The plunger assembly of claim 1, wherein the radially outer surface of the annular flange comprises a chamfered boss along at least a portion of the circumference thereof, the boss being angled to match a slope of the conical mating surface.

3. The plunger assembly of claim 1, wherein the plunger rod head further comprises at least one supporting member extending radially from a portion of the plunger rod head, and wherein a surface of the at least one supporting member is sized and adapted to contact at least a portion of the conical mating surface of the stopper adapter to restrict radial movement of the plunger rod relative to the stopper adapter.

4. The plunger assembly of claim 3, wherein the at least one supporting member is an angled rib having an angle that corresponds to a slope of the conical cavity.

5. The plunger assembly of claim 1, wherein as the plunger rod head is moved axially within the cavity of the stopper adapter, the first restraining member of the stopper adapter deforms the second restraining member of the plunger rod head, and once the plunger rod head is advanced beyond the first restraining member of the stopper adapter, the second restraining member returns to an un-deformed position to secure the plunger rod head within the aperture.

6. The plunger assembly of claim 1, wherein the second restraining member of the plunger rod head is a deformable restraining member transitionable between a deformed position and an un-deformed position.

7. The plunger assembly of claim 6, wherein the second restraining member comprises at least one deformable finger.

8. The plunger assembly of claim 6, wherein the second restraining member comprises a plurality of deformable fingers disposed about a perimeter of the plunger rod.

9. The plunger assembly of claim 8, wherein at least one of the plurality of deformable fingers includes an anti-nesting rib extending inward from an inner surface of the plurality of deformable fingers for preventing the plunger rod head from nesting within another plunger rod head.

10. The plunger assembly of claim 8, wherein as the plunger rod head is moved axially within the cavity of the stopper adapter, the first restraining member of the stopper adapter compresses the plurality of deformable fingers of the second restraining member, and once the plunger rod head is moved over and past the first restraining member of the stopper adapter, the plurality of deformable fingers of the second restraining member return to an un-deformed position such that the first restraining member of the stopper adapter engages the plurality of deformable fingers of the second restraining member thereby securing the plunger rod to the stopper adapter.

11. The plunger assembly of claim 1, wherein the first restraining member of the stopper adapter comprises a plurality of deformable fingers extending into a cavity of the stopper adapter adjacent to the aperture.

12. The plunger assembly of claim 1, wherein the second restraining member of the plunger rod head is substantially rigid.

13. The plunger assembly of claim 11, wherein as the plunger rod head is moved axially within the aperture of the stopper adapter, the second restraining member of the plunger rod head deforms the plurality of deformable fingers of the first restraining member of the stopper adapter, and once the plunger rod head is moved over and past the first restraining member of the stopper adapter, the plurality of deformable fingers of the first restraining member return to an un-deformed position such that the plurality of deformable fingers of the first restraining member engages the second restraining member thereby securing the plunger rod to the stopper adapter.

14. The plunger assembly of claim 1, wherein the stopper adapter is integrally formed with a stopper, which is adapted to slide through a barrel of a syringe.

15. The plunger assembly of claim 14, wherein the stopper includes a cavity accessible through an aperture of the stopper, and wherein the stopper adapter is positioned entirely within the cavity.

16. The plunger assembly of claim 15, wherein the stopper and the stopper adapter are formed by a two shot molding process.

17. The plunger assembly of claim 1, wherein the stopper adapter is connected to a stopper, the stopper being adapted to advance through a syringe barrel.

18. The plunger assembly of claim 17, wherein the stopper adapter comprises a threaded connection member extending from a distal end thereof, and wherein the threaded connection member is sized and adapted for insertion into a threaded cavity of the stopper to engage therewith.

19. A plunger assembly for a syringe assembly comprising:
    a stopper adapter comprising a sloped sidewall, which defines an aperture and a cavity having a conical mating surface, and a protruding member adjacent the aperture; and a plunger rod comprising a first end, a second end, a plunger rod head disposed adjacent the first end of the plunger rod, the plunger rod head comprising a deformable restraining member transitionable between a deformed position and an un-deformed position, and an annular flange proximal to the plunger rod head having a radially outer surface which is configured to contact a portion of the conical mating surface of the stopper adapter to restrict radial movement of the plunger rod relative to the stopper adapter when the plunger rod head is secured within the aperture, wherein as the plunger rod head is moved axially within the cavity of the stopper adapter, the protruding member of the stopper adapter deforms the deformable restraining member of the plunger rod head, and once the plunger rod head is advanced beyond the protruding member of the stopper adapter, the deformable restraining member returns to its un-deformed position to secure the plunger rod head within the cavity.

20. The plunger assembly of claim 19, wherein the radially outer surface of the annular flange comprises a chamfered boss along at least a portion of the circumference thereof, the boss being angled to match a slope of the conical mating surface.

21. The plunger assembly of claim 19, wherein the plunger rod head further comprises at least one supporting member extending radially from a portion of the plunger rod head, and wherein a surface of the at least one supporting member is sized and adapted to contact at least a portion of the conical mating surface of the stopper adapter to restrict radial movement of the plunger rod relative to the stopper adapter.

22. The plunger assembly of claim 21, wherein the at least one supporting member is an angled rib having an angle that corresponds to a slope of the conical cavity.

23. A syringe assembly comprising:
a syringe barrel having a distal end, an open proximal end, and a sidewall extending therebetween;
a stopper disposed within the barrel having a sidewall with a sliding surface adapted for sealing contact with the sidewall of the syringe barrel; and
a plunger assembly removeably connected to a proximal end of the stopper for advancing the stopper through the syringe barrel,
wherein the plunger assembly comprises:
a stopper adapter comprising a sloped sidewall, which defines an aperture and a cavity having a conical mating surface, and a first restraining member, and
a plunger rod comprising a proximal end, a distal end, a plunger rod head disposed adjacent the distal end of the plunger rod, the plunger rod head comprising a second restraining member engageable with the first restraining member of the stopper adapter, and an annular flange proximal to the plunger rod head having a radially outer surface which is configured to contact a portion of the conical mating surface of the stopper adapter to restrict radial movement of the plunger rod relative to the stopper adapter when the plunger rod head is secured within the aperture, and
wherein as the plunger rod head is moved axially within the aperture of the stopper adapter, the first restraining member of the stopper adapter engages the second restraining member of the plunger rod head to secure the plunger rod head within the aperture, such that once the plunger rod head is secured to the adapter, the plunger rod is capable of moving the stopper through the syringe barrel in a proximal or a distal direction.

* * * * *